US012678129B2

(12) United States Patent

Matsumoto

(10) Patent No.: US 12,678,129 B2
(45) Date of Patent: Jul. 14, 2026

(54) ULTRASOUND DIAGNOSTIC APPARATUS THAT ASSISTS IN PUNCTURING A BLOOD VESSEL OF A SUBJECT

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/478,949

(22) Filed: Sep. 29, 2023

(65) Prior Publication Data

US 2024/0130706 A1 Apr. 25, 2024
US 2024/0225590 A9 Jul. 11, 2024

(30) Foreign Application Priority Data

Oct. 19, 2022 (JP) .................................. 2022-167595

(51) Int. Cl.
*A61B 8/00* (2006.01)
*A61B 8/08* (2006.01)

(52) U.S. Cl.
CPC .......... *A61B 8/0891* (2013.01); *A61B 8/4245* (2013.01); *A61B 8/461* (2013.01); *A61B 8/483* (2013.01); *A61B 8/5207* (2013.01)

(58) Field of Classification Search
CPC ..... A61B 8/0891; A61B 8/4245; A61B 8/461; A61B 8/483; A61B 8/5207;
(Continued)

(56) References Cited

U.S. PATENT DOCUMENTS 10,555,696 B2 * 2/2020 Breteau ................ A61B 17/132
2003/0120154 A1 6/2003 Sauer et al.
(Continued)

FOREIGN PATENT DOCUMENTS

EP 3344146 B1 5/2020
JP 2008-545502 A 12/2008
(Continued)

OTHER PUBLICATIONS

The extended European search report issued by the European Patent Office on Mar. 6, 2024, which corresponds to European Patent Application No. 23204479.2-1126 and is related to U.S. Appl. No. 18/478,949.

(Continued)

*Primary Examiner* — Joel Lamprecht
*Assistant Examiner* — James F McDonald, III
(74) *Attorney, Agent, or Firm* — Studebaker Brackett PLLC

(57) ABSTRACT

Provided are a control method of an ultrasound diagnostic apparatus and an ultrasound diagnostic apparatus that enable a user to easily and accurately puncture a blood vessel of a subject.

An ultrasound diagnostic apparatus includes: an ultrasound probe; an image acquisition unit that acquires an ultrasound image of a blood vessel using the ultrasound probe; a blood vessel detection unit that detects the blood vessel from the ultrasound image; a blood vessel information acquisition unit that acquires blood vessel information of the blood vessel detected by the blood vessel detection unit; a needle information acquisition unit that acquires needle information of a puncture needle; a recommended insertion region calculation unit that calculates a recommended insertion region of the puncture needle on a body surface of a subject based on the blood vessel information, the needle information, and a predetermined needle insertion angle range; a monitor; and a display controller that displays the recommended insertion region calculated by the recommended insertion region calculation unit on the monitor.

18 Claims, 11 Drawing Sheets

(58) Field of Classification Search
   CPC .......... A61B 2017/3413; A61B 5/0035; A61B
                5/0077; A61B 5/743; A61B 8/0833; A61B
                8/463; A61B 17/3403; A61B 8/0841;
                A61B 5/489; G16H 40/63
   See application file for complete search history.

(56)                References Cited

U.S. PATENT DOCUMENTS

| | | | |
|---|---|---|---|
| 2008/0221519 A1 | 9/2008 | Schwach et al. | |
| 2014/0343406 A1* | 11/2014 | Damjanovic ...... | A61N 1/36017 |
| | | | 600/424 |
| 2015/0209113 A1 | 7/2015 | Burkholz et al. | |
| 2017/0056062 A1* | 3/2017 | Buljubasic ....... | A61B 5/150748 |
| 2017/0112465 A1 | 4/2017 | Takimoto et al. | |
| 2018/0168537 A1* | 6/2018 | Hsieh ................... | A61B 8/5215 |
| 2018/0325600 A1 | 11/2018 | Aoyagi | |
| 2019/0328317 A1* | 10/2019 | Mochizuki .............. | A61B 8/06 |
| 2020/0069330 A1* | 3/2020 | Butki ................. | A61B 17/3403 |
| 2020/0230391 A1* | 7/2020 | Burkholz ............... | A61B 34/20 |
| 2020/0237403 A1* | 7/2020 | Southard ................ | A61B 8/461 |
| 2021/0378627 A1 | 12/2021 | Yarmush et al. | |
| 2022/0071593 A1* | 3/2022 | Tran ....................... | A61B 8/085 |
| 2022/0110609 A1 | 4/2022 | Matsumoto | |
| 2022/0142608 A1* | 5/2022 | Matsumoto .......... | A61B 8/0841 |
| 2022/0160434 A1* | 5/2022 | Messerly ............... | A61B 5/062 |
| 2023/0293145 A1 | 9/2023 | Matsumoto | |

FOREIGN PATENT DOCUMENTS

| | | | | | |
|---|---|---|---|---|---|
| JP | 2009-125280 | A | 6/2009 | | |
| JP | 2014-111083 | A | 6/2014 | | |
| JP | 2014-221175 | A | 11/2014 | | |
| JP | 6487455 | B2 | 3/2019 | | |
| JP | 2019-188005 | A | 10/2019 | | |
| JP | 2022-504768 | A | 1/2022 | | |
| KR | 10-2022-0010367 | A | 1/2022 | | |
| WO | 2021/014926 | A1 | 1/2021 | | |
| WO | 2021/033491 | A1 | 2/2021 | | |
| WO | WO-2021214101 | A1 * | 10/2021 | .......... | A61B 8/5223 |
| WO | 2022/113844 | A1 | 6/2022 | | |

OTHER PUBLICATIONS

"Notice of Reasons for Refusal" Office Action issued in JP 2022-167595; mailed by the Japanese Patent Office on May 12, 2026.

* cited by examiner

ULTRASOUND DIAGNOSTIC APPARATUS THAT ASSISTS IN PUNCTURING A BLOOD VESSEL OF A SUBJECT

CROSS-REFERENCE TO RELATED APPLICATIONS

The present application claims priority under 35 U.S.C. § 119 to Japanese Patent Application No. 2022-167595, filed on Oct. 19, 2022. The above application is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus for assisting in puncturing a blood vessel of a subject.

2. Description of the Related Art

In general, a technique is known for using a so-called ultrasound diagnostic apparatus to insert a puncture needle into a blood vessel of a subject while observing the blood vessel. In order to facilitate this technique for a user of the ultrasound diagnostic apparatus, technologies for assisting in puncturing a blood vessel have been developed, for example, as disclosed in JP2022-504768A, JP6487455B, and JP2014-221175A.

JP2022-504768A discloses that a trajectory of a puncture needle to be inserted into a subject is decided on based on an ultrasound image, orientation data of the puncture needle, and orientation data of a device that inserts the puncture needle into the subject. JP6487455B discloses that an image of a blood vessel into which a puncture needle is inserted is generated based on an ultrasound image, an optical image of a subject, and information regarding a length of the puncture needle, and that so-called augmented reality (AR) display of the generated image is performed. JP2014-221175A discloses that an ultrasound image obtained by capturing a state in which a puncture needle is inserted into a subject is superimposed and displayed on an examination position in an optical image of the subject.

SUMMARY OF THE INVENTION

Meanwhile, in general, an insertable length of a puncture needle into a subject differs depending on a manufacturer that manufactures the puncture needle, a model number of the puncture needle, and the like. An insertion angle and an insertion position at which the puncture needle can reach the blood vessel may differ depending on a type of the puncture needle even if the same blood vessel is punctured. Therefore, there may be cases where, depending on a proficiency level of a user, an appropriate insertion position on a body surface of the subject for inserting the puncture needle into the blood vessel cannot be easily decided on, and the blood vessel cannot be easily and accurately punctured, even in a case where the technologies disclosed in JP2022-504768A, JP6487455B, and JP2014-221175A are used.

The present invention has been made in order to solve such a conventional problem, and an object of the present invention is to provide an ultrasound diagnostic apparatus and a control method of an ultrasound diagnostic apparatus that enable a user to easily and accurately puncture a blood vessel of a subject.

According to the following configuration, the above-described object can be achieved.

[1] An ultrasound diagnostic apparatus that assists in puncturing a blood vessel of a subject, the ultrasound diagnostic apparatus comprising:

an ultrasound probe;

an image acquisition unit configured to continuously acquire an ultrasound image of the blood vessel using the ultrasound probe;

a blood vessel detection unit configured to detect the blood vessel from the ultrasound image;

a blood vessel information acquisition unit configured to acquire blood vessel information of the blood vessel detected by the blood vessel detection unit;

a needle information acquisition unit configured to acquire needle information of a puncture needle;

a recommended insertion region calculation unit configured to calculate a recommended insertion region of the puncture needle on a body surface of the subject based on the blood vessel information acquired by the blood vessel information acquisition unit, the needle information acquired by the needle information acquisition unit, and a predetermined needle insertion angle range;

a monitor; and a display controller configured to display the recommended insertion region calculated by the recommended insertion region calculation unit on the monitor.

[2] The ultrasound diagnostic apparatus according to [1], in which the blood vessel information acquisition unit is configured to acquire a depth and a thickness of the blood vessel as the blood vessel information.

[3] The ultrasound diagnostic apparatus according to [1] or [2], in which the display controller is configured to superimpose and display the recommended insertion region on the ultrasound image acquired by the image acquisition unit.

[4] The ultrasound diagnostic apparatus according to any one of [1] to [3], further comprising:

a puncture difficulty level calculation unit configured to calculate a puncture difficulty level in inserting the puncture needle from the recommended insertion region; and a notification unit configured to notify a user of the puncture difficulty level calculated by the puncture difficulty level calculation unit.

[5] The ultrasound diagnostic apparatus according to [4], in which the notification unit is configured to change a method of displaying the recommended insertion region on the monitor or display a message on the monitor according to the puncture difficulty level.

[6] The ultrasound diagnostic apparatus according to [4], in which the puncture difficulty level calculation unit is configured to calculate the puncture difficulty level based on the blood vessel information, the needle information, and the recommended insertion region.

[7] The ultrasound diagnostic apparatus according to [4], further comprising:

a peripheral organ recognition unit configured to recognize an organ located around the blood vessel from the ultrasound image, in which the puncture difficulty level calculation unit is configured to calculate the puncture difficulty level based on the recommended insertion region calculated by the recommended insertion region calculation unit and the organ recognized by the peripheral organ recognition unit.

[8] The ultrasound diagnostic apparatus according to any one of [1] to [7], further comprising:

a three-dimensional image generation unit configured to generate a three-dimensional image of the blood vessel based on the ultrasound image, in which the recommended insertion region calculation unit is configured to calculate the recommended insertion region in consideration of the three-dimensional image.

[9] The ultrasound diagnostic apparatus according to any one of [1] to [8], further comprising:

an optical camera configured to image the subject and the ultrasound probe to acquire an optical image, in which the display controller is configured to superimpose the recommended insertion region on the optical image and display the recommended insertion region on the monitor.

[10] The ultrasound diagnostic apparatus according to any one of [1] to [9], further comprising:

a projection mapping device configured to project the recommended insertion region calculated by the recommended insertion region calculation unit onto the body surface of the subject.

[11] The ultrasound diagnostic apparatus according to any one of [1] to [10], further comprising:

a compression detection unit configured to detect compression on the body surface of the subject by the ultrasound probe, in which the recommended insertion region calculation unit is configured to recalculate the recommended insertion region based on the blood vessel information acquired by the blood vessel information acquisition unit, in a case where the compression detection unit detects that the compression applied to the body surface of the subject is equal to or greater than a predetermined compression value.

[12] The ultrasound diagnostic apparatus according to any one of [1] to [8], further comprising:

an optical camera configured to image the subject and the puncture needle to acquire an optical image; and a puncture position determination unit configured to recognize the body surface of the subject and the puncture needle from the optical image and determine whether or not the body surface of the subject and the puncture needle, which are recognized, are located within the recommended insertion region calculated by the recommended insertion region calculation unit.

[13] The ultrasound diagnostic apparatus according to [2], in which the blood vessel information acquisition unit is configured to acquire a running state of the blood vessel in addition to the depth and the thickness of the blood vessel as the blood vessel information.

[14] A control method of an ultrasound diagnostic apparatus that assists in puncturing a blood vessel of a subject, the control method comprising:

continuously acquiring an ultrasound image of the blood vessel using an ultrasound probe;

detecting the blood vessel from the ultrasound image;

acquiring blood vessel information of the detected blood vessel;

acquiring needle information of a puncture needle;

calculating a recommended insertion region of the puncture needle on a body surface of the subject based on the acquired blood vessel information, the acquired needle information, and a predetermined needle insertion angle range; and displaying the calculated recommended insertion region on a monitor.

According to the present invention, there is provided an ultrasound diagnostic apparatus that assists in puncturing a blood vessel of a subject, the ultrasound diagnostic apparatus comprising: an ultrasound probe; an image acquisition unit that continuously acquires an ultrasound image of the blood vessel using the ultrasound probe; a blood vessel detection unit that detects the blood vessel from the ultrasound image; a blood vessel information acquisition unit that acquires blood vessel information of the blood vessel detected by the blood vessel detection unit; a needle information acquisition unit that acquires needle information of a puncture needle; a recommended insertion region calculation unit that calculates a recommended insertion region of the puncture needle on a body surface of the subject based on the blood vessel information acquired by the blood vessel information acquisition unit, the needle information acquired by the needle information acquisition unit, and a predetermined needle insertion angle range; a monitor; and a display controller that displays the recommended insertion region calculated by the recommended insertion region calculation unit on the monitor. Therefore, the user can easily and accurately puncture the blood vessel of the subject.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
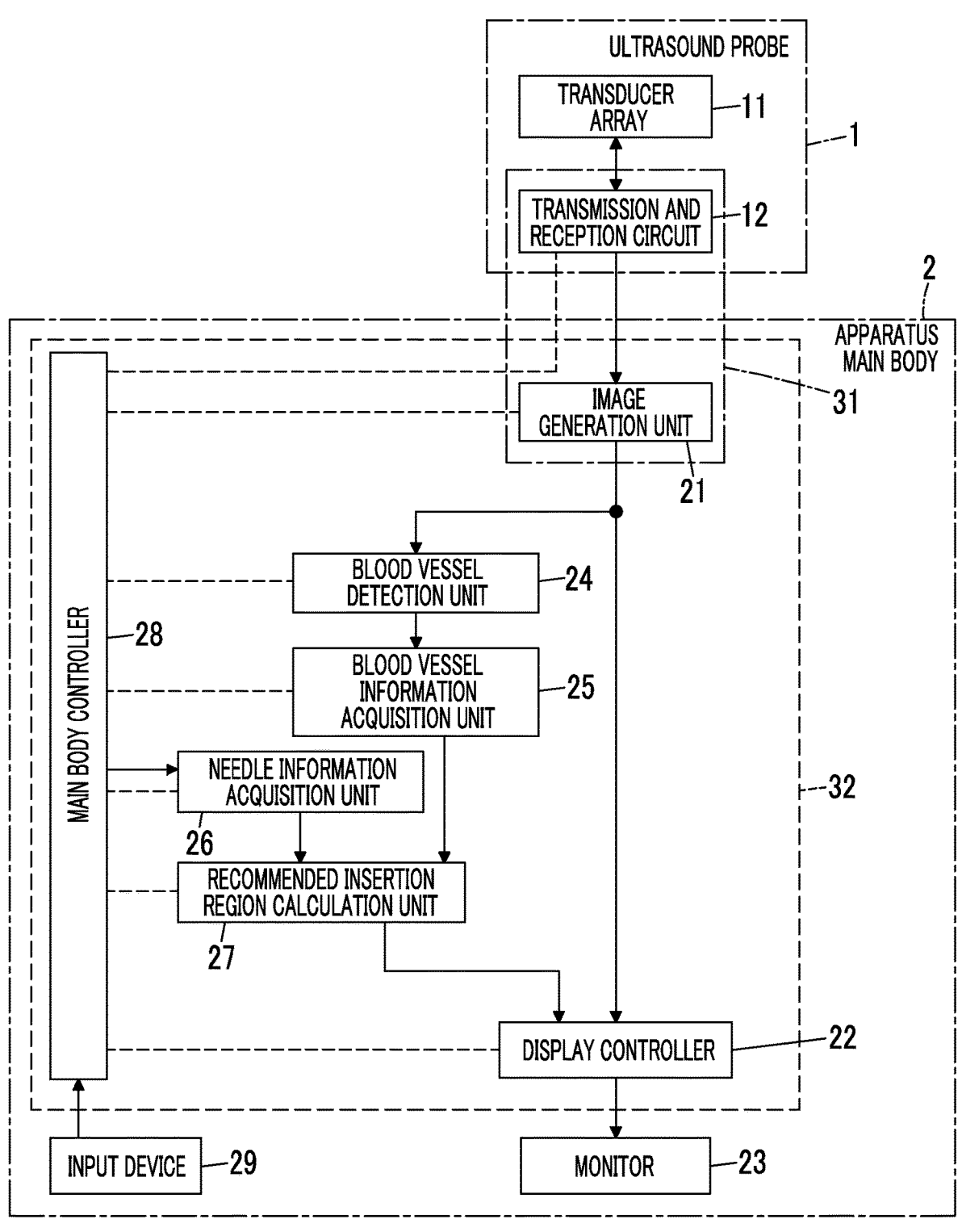
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1 and an apparatus main body 2 connected to the ultrasound probe 1. The ultrasound diagnostic apparatus is used to observe a blood vessel of a subject and assist a user of the ultrasound diagnostic apparatus in inserting a puncture needle into the blood vessel of the subject.

The ultrasound probe 1 includes a transducer array 11. A transmission and reception circuit 12 is connected to the transducer array 11.

The apparatus main body 2 includes an image generation unit 21 connected to the transmission and reception circuit 12 of the ultrasound probe 1. A display controller 22 and a monitor 23 are sequentially connected to the image generation unit 21. In addition, a blood vessel detection unit 24 is connected to the image generation unit 21. A blood vessel information acquisition unit 25 is connected to the blood vessel detection unit 24. In addition, the apparatus main body 2 comprises a needle information acquisition unit 26. A recommended insertion region calculation unit 27 is connected to the blood vessel information acquisition unit 25 and the needle information acquisition unit 26. The recommended insertion region calculation unit 27 is connected to the display controller 22. In addition, a main body controller 28 is connected to the transmission and reception circuit 12, the display controller 22, the blood vessel detection unit 24, the blood vessel information acquisition unit 25, the needle information acquisition unit 26, and the recommended insertion region calculation unit 27. An input device 29 is connected to the main body controller 28.

In addition, the transmission and reception circuit 12 and the image generation unit 21 constitute an image acquisition unit 31. Further, the image generation unit 21, the display controller 22, the blood vessel detection unit 24, the blood vessel information acquisition unit 25, the needle information acquisition unit 26, the recommended insertion region calculation unit 27, and the main body controller 28 constitute a processor 32 for the apparatus main body 2.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission and reception circuit 12 and receives an ultrasound echo from a subject to output a signal based on the ultrasound echo. For example, each ultrasound transducer is composed of a piezoelectric body consisting of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like, and electrodes formed at both ends of the piezoelectric body.

Figure 2:
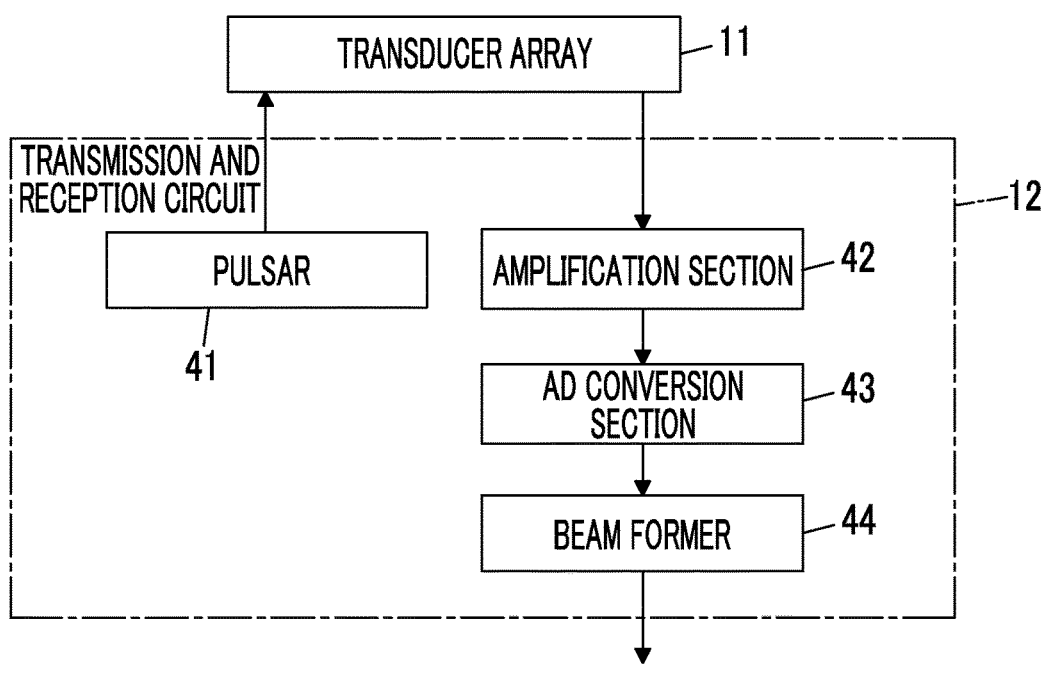
FIG. 2 is a block diagram showing a configuration of a transmission and reception circuit in Embodiment 1 of the present invention.

The transmission and reception circuit 12 causes the transducer array 11 to transmit the ultrasound wave and generates a sound ray signal on the basis of a reception signal acquired by the transducer array 11, under the control of the main body controller 28. As shown in FIG. 2, the transmission and reception circuit 12 includes a pulsar 41 connected to the transducer array 11, and an amplification section 42, an analog-to-digital (AD) conversion section 43, and a beam former 44 that are sequentially connected in series to the transducer array 11.

The pulsar 41 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 28. In this way, in a case where a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, whereby an ultrasound beam is formed from the combined wave of these ultrasound waves.

The transmitted ultrasound beam is reflected in, for example, a target such as a site of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
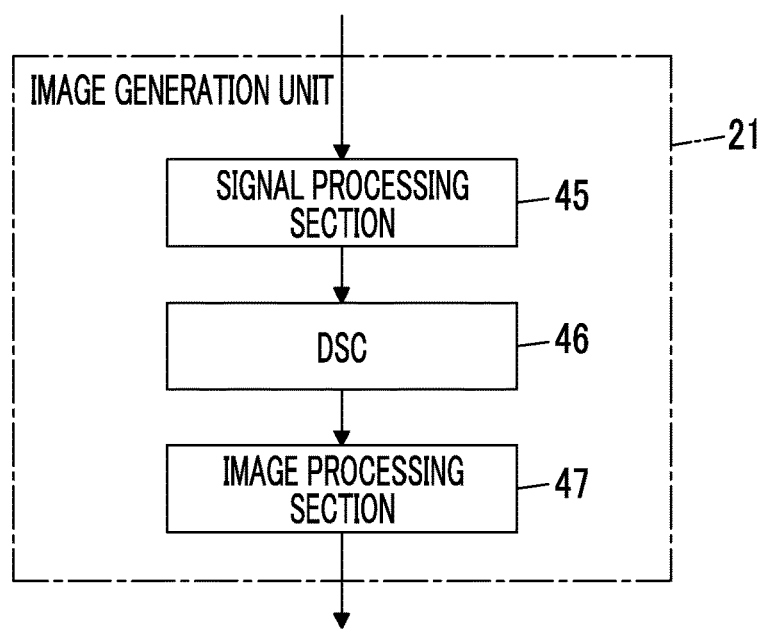
FIG. 3 is a block diagram showing a configuration of an image generation unit in Embodiment 1 of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues inside the subject, by performing, on the sound ray signal received from the transmission and reception circuit 12, correction of the attenuation due to the distance according to the depth of the reflection position of the ultrasound wave using a sound velocity value set by the main body controller 28 and then performing envelope detection processing.

The DSC 46 converts (raster-converts) the B-mode image signal generated by the signal processing section 45 into an image signal in accordance with a normal television signal scanning method.

The image processing section 47 performs various types of necessary image processing such as gradation processing on the B-mode image signal input from the DSC 46 and then sends out the B-mode image signal to the display controller 22 and the blood vessel detection unit 24. Hereinafter, the B-mode image signal that has been subjected to image processing by the image processing section 47 is referred to as an ultrasound image.

Figure 4:
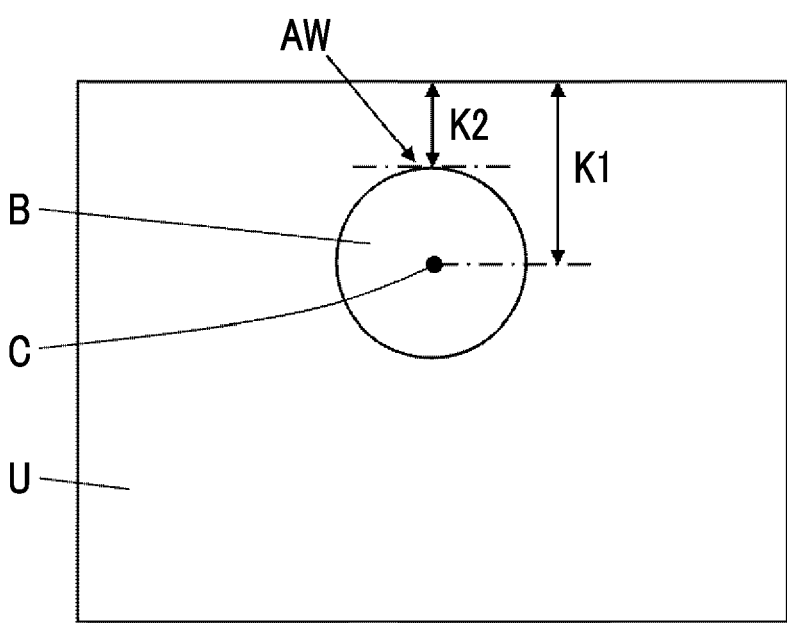
FIG. 4 is a diagram showing an example of an ultrasound image in which a blood vessel is captured.

In the present invention, for example, as shown in FIG. 4, an ultrasound image U showing a blood vessel B inside the subject is acquired. Hereinafter, unless otherwise specified, the ultrasound image U showing a short-axis image of the blood vessel B is simply referred to as the ultrasound image U showing the blood vessel B. The short-axis image of the blood vessel B refers to a cross section of the blood vessel B perpendicular to a running direction of the blood vessel B.

The display controller 22 performs predetermined processing on the ultrasound image or the like generated by the image generation unit 21 and displays the ultrasound image or the like on the monitor 23, under the control of the main body controller 28.

The monitor 23 performs various kinds of display under the control of the display controller 22. The monitor 23 can include, for example, a display device such as a liquid crystal display (LCD) or an organic electroluminescence (EL) display.

The main body controller 28 controls each unit of the apparatus main body 2 and the ultrasound probe 1 in accordance with a program recorded in advance, or the like.

The input device 29 accepts an input operation from an examiner and sends out input information to the main body controller 28. The input device 29 is composed of, for example, a device for the examiner to perform an input operation, such as a keyboard, a mouse, a trackball, a touchpad, or a touch panel.

The blood vessel detection unit 24 detects the blood vessel B shown in the ultrasound image U by analyzing the ultrasound image U. The blood vessel detection unit 24 stores a plurality of template images related to the short-axis image of the blood vessel B, and can detect the blood vessel B using a so-called template matching method of searching the ultrasound image U using the plurality of template images. The blood vessel detection unit 24 can also detect the blood vessel B from the ultrasound image U using, for example, a trained model in so-called machine learning, which has been trained using a large number of ultrasound images U showing the short-axis image of the blood vessel B.

The blood vessel information acquisition unit 25 acquires blood vessel information of the blood vessel B detected by the blood vessel detection unit 24 by analyzing the ultrasound image U based on the detection result of the blood vessel B by the blood vessel detection unit 24.

The blood vessel information acquisition unit 25 can acquire, for example, the depth of the blood vessel B as the blood vessel information. In this case, the blood vessel information acquisition unit 25 can calculate the depth of the blood vessel B, for example, by detecting a center C of the blood vessel B and measuring a distance K1 from a position of a body surface of the subject, that is, from a shallowest position of the ultrasound image U, to the center C of the blood vessel B. Alternatively, the blood vessel information acquisition unit 25 can also calculate the depth of the blood vessel B, for example, by detecting a position of an anterior wall AW in the blood vessel B and measuring a distance K2 from the position of the body surface of the subject to the position of the anterior wall AW of the blood vessel B. The anterior wall AW of the blood vessel B means a blood vessel wall disposed at the shallowest position in the blood vessel B.

In addition, the blood vessel information acquisition unit 25 can also calculate, for example, the thickness of the blood vessel B as the blood vessel information. In addition, in a case where a plurality of frames of ultrasound images U are continuously generated by the image generation unit 21 while the ultrasound probe 1 is moved along a running direction of the blood vessel B, the blood vessel information acquisition unit 25 can also acquire a running state of the blood vessel B as the blood vessel information by analyzing the plurality of continuous frames of ultrasound images U.

Meanwhile, in general, an insertable length of the puncture needle into the subject may differ depending on a manufacturer that manufactures the puncture needle, a model number of the puncture needle, and the like. The needle information acquisition unit 26 acquires needle information of the puncture needle, including at least the insertable length of the puncture needle into the subject, based on information input from the user via, for example, the input device 29. In this case, the needle information acquisition unit 26 can acquire the insertable length of the puncture needle input from the user as the needle information. In addition, the needle information acquisition unit 26 can also acquire the needle information by storing pieces of needle information of a plurality of types of puncture needles in advance and selecting needle information of the puncture needle related to the input of the user from among the pieces of needle information of the plurality of types of puncture needles based on information such as the manufacturer, the model number, or the name of the puncture needle.

Meanwhile, there may be cases where the tip of the puncture needle cannot reach the depth of the blood vessel B depending on the relationship between the insertable length of the puncture needle into the subject and the insertion angle of the puncture needle. The recommended insertion region calculation unit 27 sets a needle insertion angle range in which the puncture needle can reach the blood vessel B based on the blood vessel information acquired by the blood vessel information acquisition unit 25 and the needle information acquired by the needle information acquisition unit 26, and calculates a recommended insertion region of the puncture needle on the body surface of the subject based on the blood vessel information, the needle information, and the needle insertion angle range.

Figure 5:
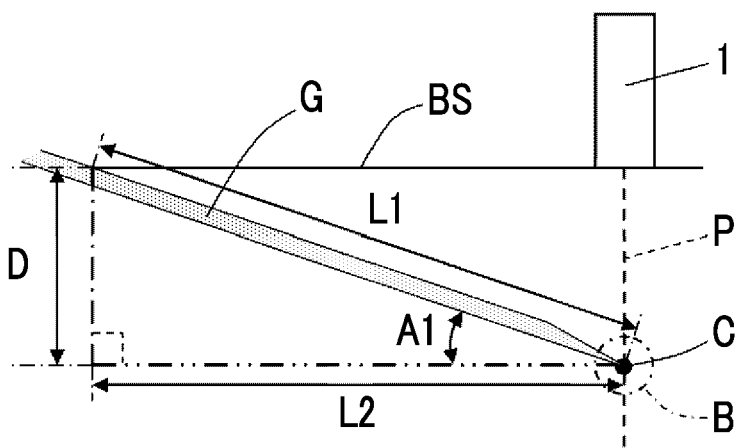
FIG. 5 is a diagram schematically showing a relationship between an insertable length of a puncture needle, an insertion angle of the puncture needle, an insertion depth of a tip of the puncture needle, and an insertion position of the puncture needle.

The recommended insertion region calculation unit 27 can set a predetermined angle, for example, 45 degrees or the like, as an upper limit value A2 of the needle insertion angle range. In addition, in a case of setting a lower limit value A1 of the needle insertion angle range, as shown in FIG. 5, the recommended insertion region calculation unit 27 calculates $\arcsin(D/L1)$ with the insertable length of a puncture needle G into the subject as L1 and the depth of the blood vessel B from a body surface BS of the subject as D. Then, the recommended insertion region calculation unit 27 can set the lower limit value A1 of the needle insertion angle range by calculating arcsin(D/L1) in a case where the depth D<the length L1 is satisfied and arcsin(D/L1) is less than the upper limit value A2 of the needle insertion angle range. Here, "arcsin" represents an inverse function of a so-called sine function.

In addition, the recommended insertion region calculation unit 27 calculates a distance L2 shown in FIG. 5 through D/[tan(A1)] using the set lower limit value A1 of the needle insertion angle range, and calculates a distance L3 (not shown) through D/[tan(A2)] using the set upper limit value A2 of the needle insertion angle range. Here, "tan" represents a so-called tangent function. The recommended insertion region calculation unit 27 can calculate a region between a position separated by the distance L2 and a position separated by the distance L3 from the tomographic plane P corresponding to the ultrasound image U analyzed by the blood vessel detection unit 24 and the blood vessel information acquisition unit 25, that is, a region between the position separated by the distance L2 and the position separated by the distance L3 from the tip part of the ultrasound probe 1, as the recommended insertion region.

The recommended insertion region calculated in this manner represents a range of a puncture position on the body surface BS of the subject, in which the puncture needle G currently in use can reach the depth D of the blood vessel B, in a case where the puncture needle G is inserted into the subject within the needle insertion angle range.

Figure 6:
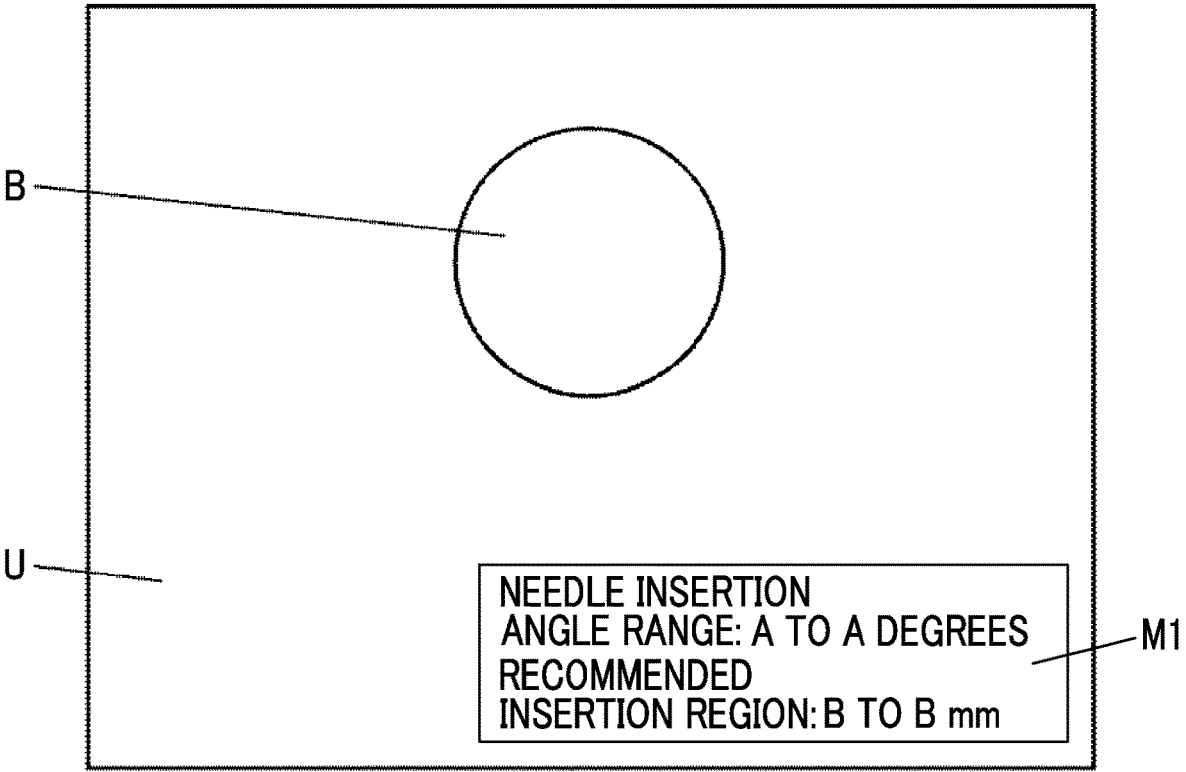
FIG. 6 is a diagram showing a display example of a recommended insertion region.

The display controller 22 can display the recommended insertion region calculated by the recommended insertion region calculation unit 27 on the monitor 23, for example, as shown in FIG. 6, through a message M1 together with the ultrasound image U. In the example of FIG. 6, the message M1 including the needle insertion angle range and the recommended insertion region is displayed by being superimposed on the ultrasound image U. The user can easily insert the puncture needle G into the blood vessel B regardless of the proficiency level by inserting the puncture needle G into the subject while confirming the recommended insertion region displayed on the monitor 23.

Although the processor 32 including the image generation unit 21, the display controller 22, the blood vessel detection unit 24, the blood vessel information acquisition unit 25, the needle information acquisition unit 26, the recommended insertion region calculation unit 27, and the main body controller 28 is composed of a central processing unit (CPU) and a control program for causing the CPU to perform various types of processing, the processor 32 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the blood vessel detection unit 24, the blood vessel information acquisition unit 25, the needle information acquisition unit 26, the recommended insertion region calculation unit 27, and the main body controller 28 of the processor 32 can also be configured by being integrated partially or entirely into one CPU or the like.

Next, an example of the operation of the ultrasound diagnostic apparatus according to Embodiment 1 will be described using the flowchart of FIG. 7.

First, in step S1, the ultrasound images U showing the blood vessel B of the subject in a state in which the user disposes the ultrasound probe 1 on the body surface BS of the subject is acquired. In this case, the transducer array 11 of the ultrasound probe 1 transmits the ultrasound beam into the subject and receives the ultrasound echo from the inside of the subject, thereby generating the reception signal. The transmission and reception circuit 12 of the image acquisition unit 31 performs so-called reception focus processing on the reception signal to generate the sound ray signal, under the control of the main body controller 28. The sound ray signal generated by the transmission and reception circuit 12 is sent out to the image generation unit 21. The image generation unit 21 generates the ultrasound image U using the sound ray signal sent out from the transmission and reception circuit 12.

Next, in step S2, the blood vessel detection unit 24 analyzes the ultrasound image U acquired in step S1 to detect the blood vessel B shown in the ultrasound image U. In this case, the blood vessel detection unit 24 can detect the blood vessel B using, for example, a template matching method and can also detect the blood vessel B using a trained model that has been trained using a large number of ultrasound images U showing the blood vessel B.

In step S3, the blood vessel information acquisition unit 25 acquires the blood vessel information including at least the depth D of the blood vessel B detected in step S2. In this case, the blood vessel information acquisition unit 25 can measure the depth of the center C of the blood vessel B or the depth of the anterior wall AW of the blood vessel B as the depth D of the blood vessel B by analyzing the ultrasound image U.

In step S4, the needle information acquisition unit 26 acquires the needle information of the puncture needle G used to puncture the subject. In this case, the needle information acquisition unit 26 can acquire the needle information based on information input from the user via, for example, the input device 29.

In step S5, the recommended insertion region calculation unit 27 sets the needle insertion angle range based on the blood vessel information acquired in step S3 and the needle information acquired in step S4, and calculates the recommended insertion region based on the blood vessel information, the needle information, and the needle insertion angle range.

In this case, the recommended insertion region calculation unit 27 can set the lower limit value A1 of the needle insertion angle range based on, for example, the depth D of the blood vessel B calculated in step S3 and the insertable length L1 of the puncture needle G into the subject, which is calculated in step S4, and can set a predetermined angle such as 45 degrees as the upper limit value A2 of the needle insertion angle range. Further, the recommended insertion region calculation unit 27 can calculate, as the recommended insertion region, the region between the position separated by the distance L2 and the position separated by the distance L3 from the tip part of the ultrasound probe 1 by calculating the distance L2 shown in FIG. 5 using D/[tan(A1)] and calculating the distance L3 (not shown) using D/[tan(A2)].

The recommended insertion region calculated in this manner represents a range of a puncture position on the body surface BS of the subject, in which the puncture needle G currently in use can reach the depth D of the blood vessel B, in a case where the puncture needle G is inserted into the subject within the needle insertion angle range.

Finally, in step S6, the display controller 22 displays the recommended insertion region calculated in step S5 on the monitor 23, for example, as shown in FIG. 6, through the message M1. The user can easily insert the puncture needle G into the blood vessel B regardless of the proficiency level by puncturing the subject while confirming the message M1.

Figure 7:
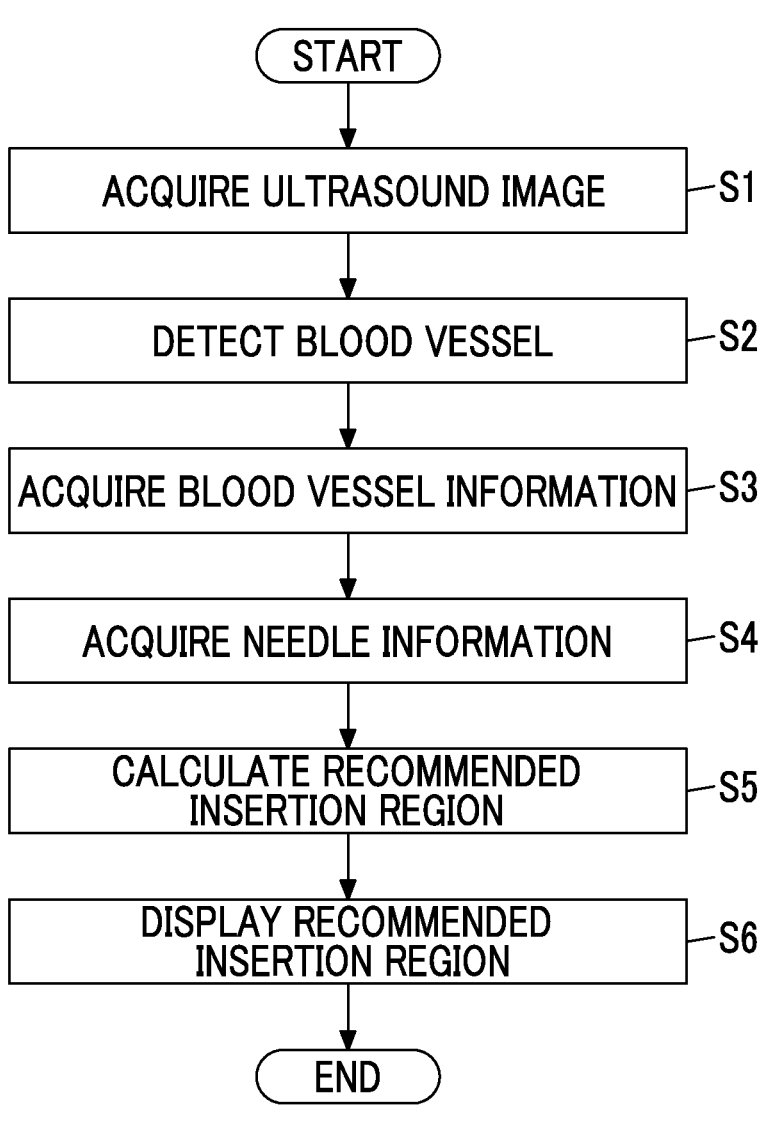
FIG. 7 is a flowchart showing an operation of the ultrasound diagnostic apparatus according to Embodiment 1 of the present invention.

In a case where the processing of step S6 is completed in this manner, the operation of the ultrasound diagnostic apparatus according to the flowchart of FIG. 7 is completed.

From the above, with the ultrasound diagnostic apparatus of Embodiment 1, the blood vessel detection unit 24 detects the blood vessel B of the subject shown in the ultrasound image U, the blood vessel information acquisition unit 25 acquires the blood vessel information of the detected blood vessel B, the needle information acquisition unit 26 acquires the needle information of the puncture needle G to be inserted into the subject, the recommended insertion region calculation unit 27 calculates the recommended insertion region of the puncture needle G on the body surface BS of the subject based on the blood vessel information, the needle information, and the needle insertion angle range, and the display controller 22 displays the recommended insertion region on the monitor 23. Therefore, the user can easily and accurately puncture the blood vessel B of the subject regardless of the proficiency level by inserting the puncture needle G into the subject while confirming the recommended insertion region displayed on the monitor 23.

Although it has been described that the transmission and reception circuit 12 is provided in the ultrasound probe 1, the transmission and reception circuit 12 may be provided in the apparatus main body 2.

In addition, although it has been described that the image generation unit 21 is provided in the apparatus main body 2, the image generation unit 21 may be provided in the ultrasound probe 1.

Further, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

In addition, in a case where the thickness of the blood vessel B is acquired as the blood vessel information by the blood vessel information acquisition unit 25, the recommended insertion region calculation unit 27 can also calculate the recommended insertion region in consideration of the thickness of the blood vessel B. In general, it may be difficult to puncture a thin blood vessel B. Therefore, the recommended insertion region calculation unit 27 can calculate, for example, a region in which the needle can reach within a portion where the blood vessel B has a thickness equal to or greater than a predetermined thickness, within the region between the position separated by the distance L2 and the position separated by the distance L3 from the tip part of the ultrasound probe 1, as the recommended insertion region.

In addition, in a case where the running state of the blood vessel B is acquired as the blood vessel information by the blood vessel information acquisition unit 25, the recommended insertion region calculation unit 27 can also calculate the recommended insertion region in consideration of the running state of the blood vessel B. In general, the blood vessel B may run with curvature toward the deep side or the shallow side of the subject, and for example, there is a risk that the puncture needle G may penetrate through the blood vessel B depending on the insertion angle of the puncture needle G. In that respect, the recommended insertion region calculation unit 27 can calculate, for example, a region in which the needle can reach within a portion where a change rate of the position of the blood vessel B in the depth direction is equal to or less than a predetermined change rate, within the region between the position separated by the distance L2 and the position separated by the distance L3 from the tip part of the ultrasound probe 1, as the recommended insertion region.

Further, although it has been described that the needle information acquisition unit 26 acquires the needle information based on the information input from the user via the input device 29, the method of acquiring the needle information is not limited to this. For example, the needle information acquisition unit 26 can also automatically acquire the needle information by storing the pieces of needle information of the plurality of types of puncture needles G in advance, by analyzing the optical image of the puncture needle G, which is used to puncture the subject, to recognize the type of the puncture needle G, and then by selecting needle information corresponding to the puncture needle G recognized from the stored pieces of needle information of the plurality of types of puncture needles G. In this case, the needle information acquisition unit 26 can recognize the puncture needle G using, for example, a template matching method. The needle information acquisition unit 26 can also recognize the puncture needle G by using a trained model that has been trained using a large number of optical images showing the plurality of types of puncture needles G.

Further, in a case where a two-dimensional code such as a barcode, or a marker for identifying the puncture needle G is attached to the puncture needle G, the needle information acquisition unit 26 can also recognize the type of the puncture needle G, for example, by analyzing the optical image of the puncture needle G and reading the two-dimensional code, the marker, or the like.

Embodiment 2

Usually, the shape of the blood vessel B varies depending on the site of the subject and the subject, and various organs are located around the blood vessel B. Therefore, a difficulty level of puncture may be high depending on the position of the blood vessel B. The ultrasound diagnostic apparatus of the embodiment of the present invention can calculate the difficulty level of puncture for the observed blood vessel B such that the user can easily puncture the blood vessel B while avoiding a portion having a high difficulty level.

Figure 8:
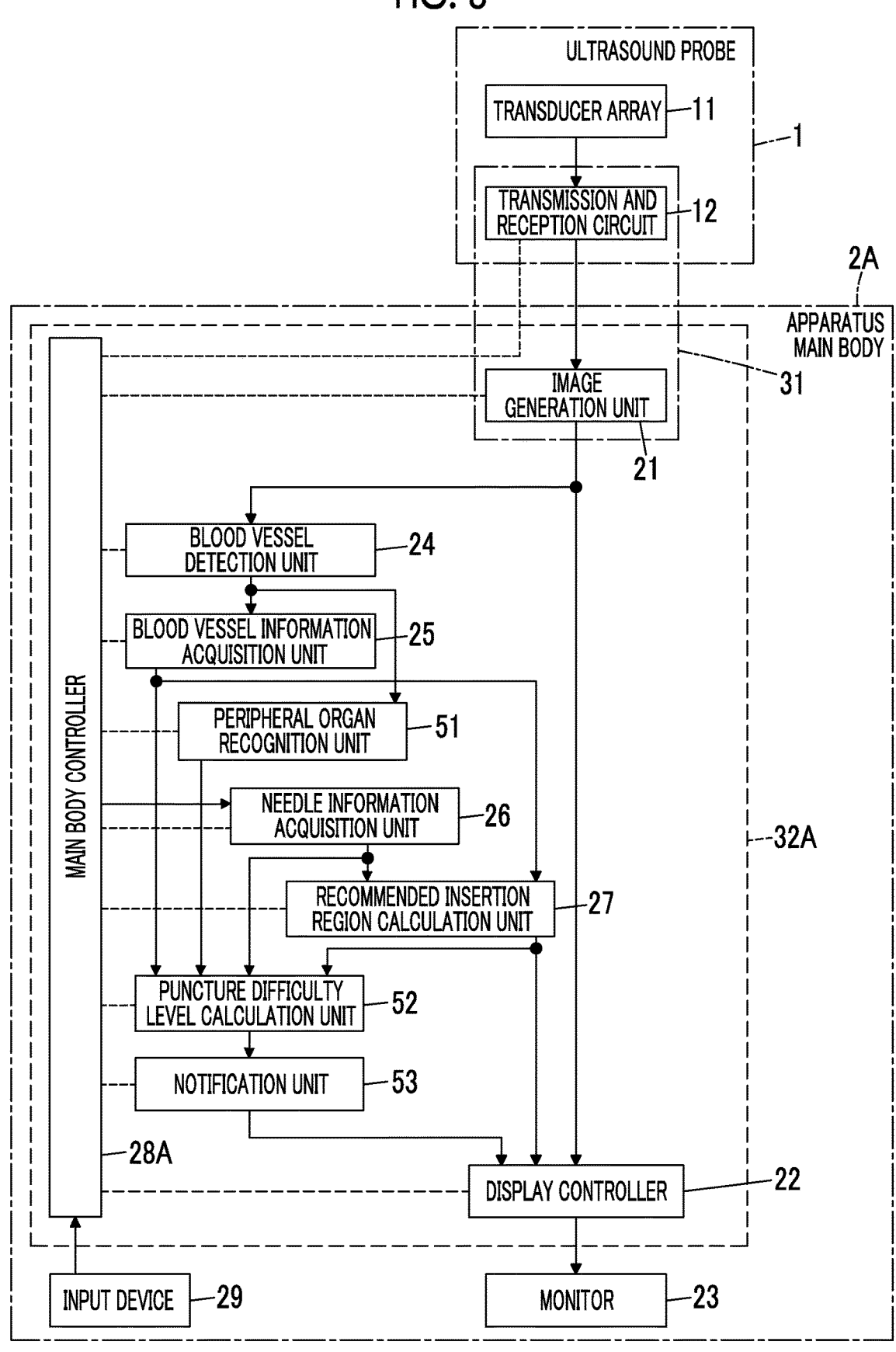
FIG. 8 is a block diagram showing a configuration of an ultrasound diagnostic apparatus according to Embodiment 2 of the present invention.

FIG. 8 shows a configuration of an ultrasound diagnostic apparatus of Embodiment 2. The ultrasound diagnostic apparatus of Embodiment 2 comprises an apparatus main body 2A instead of the apparatus main body 2 with respect to the ultrasound diagnostic apparatus of Embodiment 1 shown in FIG. 1. The apparatus main body 2A further comprises a peripheral organ recognition unit 51, a puncture difficulty level calculation unit 52, and a notification unit 53 and comprises a main body controller 28A instead of the main body controller 28, with respect to the apparatus main body 2 in Embodiment 1.

In the apparatus main body 2A, the peripheral organ recognition unit 51 is connected to the blood vessel detection unit 24 and the main body controller 28A. The puncture difficulty level calculation unit 52 is connected to the blood vessel information acquisition unit 25, the needle information acquisition unit 26, the recommended insertion region calculation unit 27, the peripheral organ recognition unit 51, and the main body controller 28A. The notification unit 53 is connected to the puncture difficulty level calculation unit 52 and the main body controller 28A. The notification unit 53 is connected to the display controller 22.

Further, the image generation unit 21, the display controller 22, the blood vessel detection unit 24, the blood vessel information acquisition unit 25, the needle information acquisition unit 26, the recommended insertion region calculation unit 27, the main body controller 28A, the peripheral organ recognition unit 51, the puncture difficulty level calculation unit 52, and the notification unit 53 constitute a processor 32A for the apparatus main body 2A.

The peripheral organ recognition unit 51 analyzes the ultrasound image U generated by the image generation unit 21 to recognize an organ located around the blood vessel B detected by the blood vessel detection unit 24. The peripheral organ recognition unit 51 stores a plurality of template images related to a plurality of types of organs of the subject, and can detect the organ located around the blood vessel B using a template matching method of searching the ultrasound image U using the plurality of template images. The peripheral organ recognition unit 51 can also detect the organ located around the blood vessel B from the ultrasound image U using, for example, a trained model that has been trained using a large number of ultrasound images U showing the organ located around the blood vessel B.

The puncture difficulty level calculation unit 52 calculates the puncture difficulty level in inserting the puncture needle G from the recommended insertion region calculated by the recommended insertion region calculation unit 27. For example, the puncture difficulty level calculation unit 52 has, for example, an angle threshold value set to 30 degrees or the like for the lower limit value A1 of the needle insertion angle range set by the recommended insertion region calculation unit 27, and can calculate the puncture difficulty level in a case where the lower limit value A1 of the needle insertion angle range is equal to or less than the angle threshold value as "easy" and can calculate the puncture difficulty level in a case where the lower limit value A1 of the needle insertion angle range is equal to or greater than the angle threshold value as "difficult".

In addition, the puncture difficulty level calculation unit 52 can calculate the puncture difficulty level based on, for example, the blood vessel information acquired by the blood vessel information acquisition unit 25, the needle information acquired by the needle information acquisition unit 26, and the recommended insertion region calculated by the recommended insertion region calculation unit 27. In this case, for example, the puncture difficulty level calculation unit 52 can calculate a lower puncture difficulty level for a thicker blood vessel B, and can calculate a higher puncture difficulty level for a thinner blood vessel B. In addition, for example, the puncture difficulty level calculation unit 52 can calculate a lower puncture difficulty level for a portion where the change rate of the shape and the position of the blood vessel B is smaller, and can calculate a higher puncture difficulty level for a portion where the change rate of the shape and the position of the blood vessel B is larger. In addition, the puncture difficulty level calculation unit 52 can calculate a low or high puncture difficulty level depending on the type of the puncture needle G to be used.

In addition, the puncture difficulty level calculation unit 52 can calculate the puncture difficulty level based on the recommended insertion region calculated by the recommended insertion region calculation unit 27 and the organ recognized by the peripheral organ recognition unit 51. For example, the puncture difficulty level calculation unit 52 can calculate a high puncture difficulty level in a case where an organ is recognized in the vicinity of the blood vessel B, and can calculate a low puncture difficulty level in a case where an organ is not recognized in the vicinity of the blood vessel B.

In addition, the puncture difficulty level calculation unit 52 can calculate a low or high puncture difficulty level depending on the type of the organ recognized by the peripheral organ recognition unit 51. In this case, the puncture difficulty level calculation unit 52 can calculate a high puncture difficulty level, for example, in a case where the peripheral organ recognition unit 51 recognizes an artery, for which puncture avoidance is recommended, in the vicinity of the vein as a puncture target.

The notification unit 53 notifies the user of the puncture difficulty level calculated by the puncture difficulty level calculation unit 52. The notification unit 53 can display, for example, a message indicating the puncture difficulty level in a stepwise manner, such as "easy" and "difficult", on the monitor 23. In addition, for example, the notification unit 53 can also change the method of displaying the recommended insertion region on the monitor 23 according to the puncture difficulty level, such as changing the display color of the recommended insertion region according to the puncture difficulty level, making the display of the recommended insertion region blink according to the puncture difficulty level, or changing the color or the thickness of the contour of the recommended insertion region according to the puncture difficulty level.

From the above, with the ultrasound diagnostic apparatus of Embodiment 2, the puncture difficulty level calculation unit 52 calculates the puncture difficulty level based on the recommended insertion region and at least one of the blood vessel information, the needle information, or the organ around the blood vessel B recognized by the peripheral organ recognition unit 51, and the notification unit 53 notifies the user of the puncture difficulty level. Therefore, the user can easily and accurately puncture the blood vessel B of the subject while avoiding, for example, a portion having a high puncture difficulty level.

Although it has been described that the peripheral organ recognition unit 51 recognizes the organ around the blood vessel B, it is also possible to recognize, for example, an avoidance-recommended target object, which is located around the blood vessel B and for which puncture should be avoided, such as nerves around the blood vessel B and lesion parts around the blood vessel B. In this case, for example, the puncture difficulty level calculation unit 52 can calculate a high puncture difficulty level in a case where the avoidance-recommended target object is recognized around the blood vessel B, and can calculate a low puncture difficulty level in a case where the avoidance-recommended target object is not recognized around the blood vessel B. As a result, the user can easily and accurately puncture the blood vessel B of the subject while avoiding the avoidance-recommended target object by confirming the puncture difficulty level obtained through the notification from the notification unit 53.

Further, although it has been described that the notification unit 53 notifies the user of the puncture difficulty level through the display on the monitor 23, the method of notifying the user is not limited to this. For example, in a case where the ultrasound diagnostic apparatus comprises a speaker (not shown), the notification unit 53 can also notify the user of the puncture difficulty level by sound via the speaker.

Embodiment 3

The ultrasound diagnostic apparatus can also calculate the recommended insertion region in consideration of the detailed shape of the blood vessel B based on a three-dimensional image of the blood vessel B.

Figure 9:
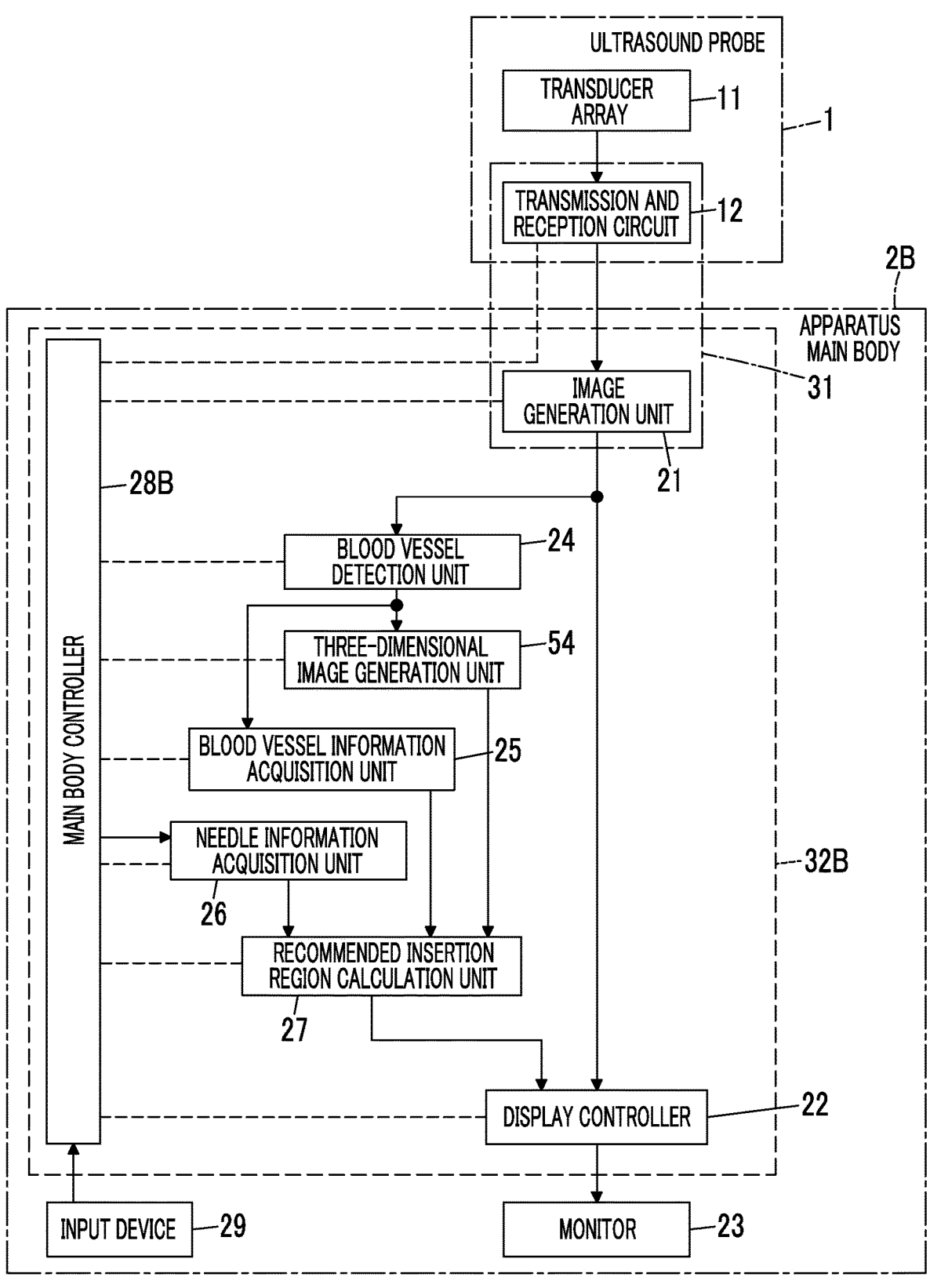
FIG. 9 is a block diagram showing a configuration of an ultrasound diagnostic apparatus according to Embodiment 3 of the present invention.

FIG. 9 shows a configuration of an ultrasound diagnostic apparatus of Embodiment 3. The ultrasound diagnostic apparatus of Embodiment 3 comprises an apparatus main body 2B instead of the apparatus main body 2 with respect to the ultrasound diagnostic apparatus of Embodiment 1 shown in FIG. 1. The apparatus main body 2B further comprises a three-dimensional image generation unit 54 and comprises a main body controller 28B instead of the main body controller 28, with respect to the apparatus main body 2 in Embodiment 1.

In the apparatus main body 2B, the three-dimensional image generation unit 54 is connected to the blood vessel detection unit 24 and the main body controller 28B. The three-dimensional image generation unit 54 is connected to the recommended insertion region calculation unit 27. Further, the image generation unit 21, the display controller 22, the blood vessel detection unit 24, the blood vessel information acquisition unit 25, the needle information acquisition unit 26, the recommended insertion region calculation unit 27, the main body controller 28B, and the three-dimensional image generation unit 54 constitute a processor 32B for the apparatus main body 2B.

The three-dimensional image generation unit 54 generates a three-dimensional image of the blood vessel B detected by the blood vessel detection unit 24 based on the plurality of frames of continuous ultrasound images U that are generated by the image generation unit 21 while the ultrasound probe 1 is moved along the running direction of the blood vessel B. This three-dimensional image shows in detail the shape of the blood vessel B and the positional change of the blood vessel B in three dimensions.

The recommended insertion region calculation unit 27 calculates the recommended insertion region in consideration of the three-dimensional image of the blood vessel B generated by the three-dimensional image generation unit 54. The recommended insertion region calculation unit 27 can calculate the recommended insertion region, for example, by excluding a region in which the needle may reach within a portion of the blood vessel B having a complexly changed shape, and a region in which the needle may reach within a portion of the blood vessel B having an abnormal shape, such as a thickened portion, within the region between the position separated by the distance L2 and the position separated by the distance L3 from the tip part of the ultrasound probe 1.

From the above, with the ultrasound diagnostic apparatus of Embodiment 3, the three-dimensional image generation unit 54 generates the three-dimensional image of the blood vessel B, and the recommended insertion region calculation unit 27 calculates the recommended insertion region that reflects the detailed shape of the blood vessel B, in consideration of the three-dimensional image of the blood vessel B. Therefore, the user can easily and safely puncture the blood vessel B.

The ultrasound diagnostic apparatus of Embodiment 3 has a configuration in which the three-dimensional image generation unit 54 is added to the ultrasound diagnostic apparatus of Embodiment 1, but a configuration can also be employed in which the three-dimensional image generation unit 54 is added to the ultrasound diagnostic apparatus of Embodiment 2.

Embodiment 4

The ultrasound diagnostic apparatus of the embodiment of the present invention can also superimpose and display the recommended insertion region on the optical image obtained by capturing the subject such that the user can easily grasp the recommended insertion region on the body surface BS of the subject.

Figure 10:
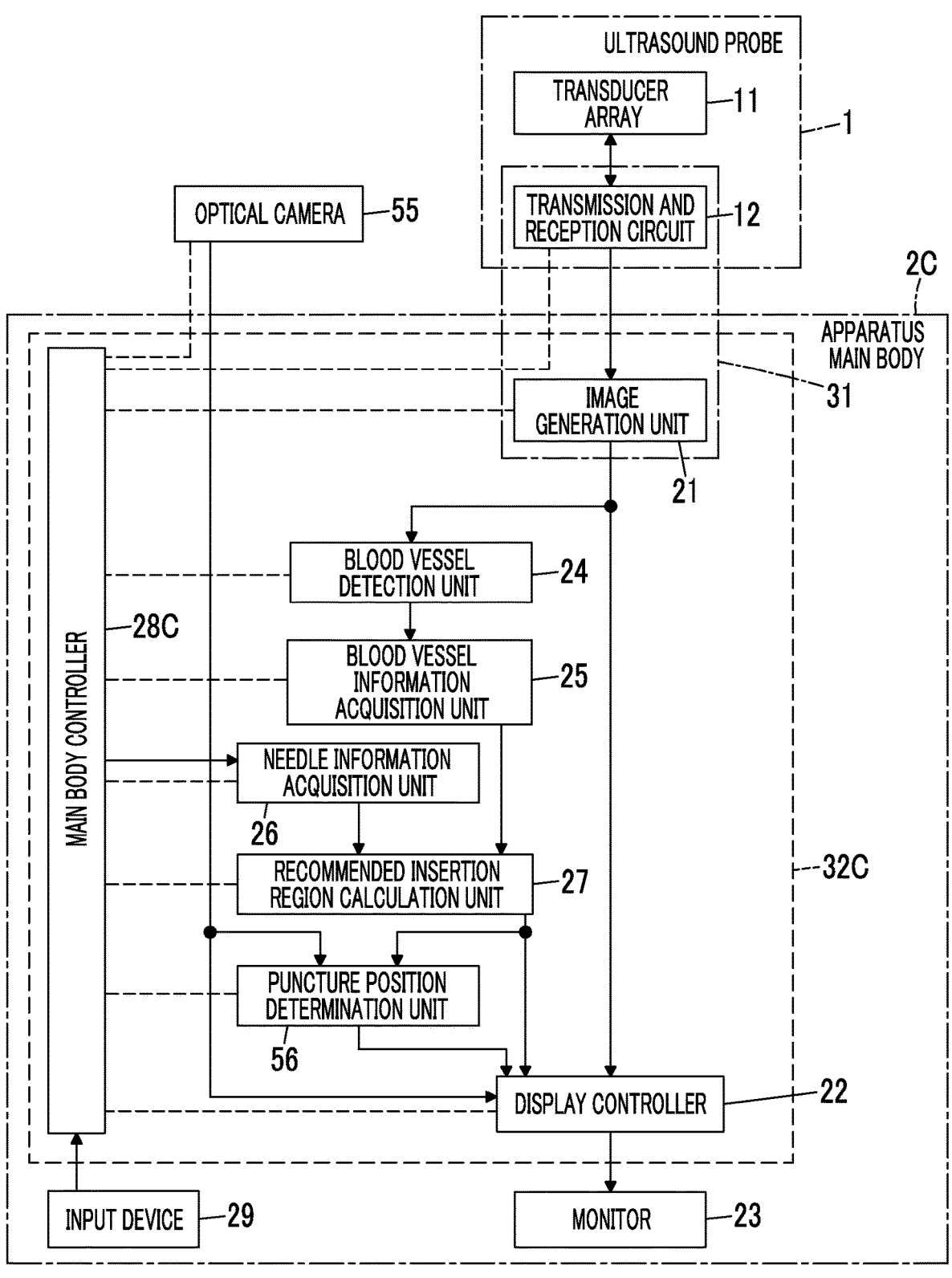
FIG. 10 is a block diagram showing a configuration of an ultrasound diagnostic apparatus according to Embodiment 4 of the present invention.

FIG. 10 shows a configuration of an ultrasound diagnostic apparatus of Embodiment 4. The ultrasound diagnostic apparatus of Embodiment 4 further comprises an optical camera 55 and comprises an apparatus main body 2C instead of the apparatus main body 2, with respect to the ultrasound diagnostic apparatus of Embodiment 1 shown in FIG. 1. The apparatus main body 2C further comprises a puncture position determination unit 56 and comprises a main body controller 28C instead of the main body controller 28, with respect to the apparatus main body 2 in Embodiment 1.

The optical camera 55 is connected to the display controller 22 and the main body controller 28. Further, in the apparatus main body 2C, the puncture position determination unit 56 is connected to the recommended insertion region calculation unit 27, the optical camera 55, and the main body controller 28C. The puncture position determination unit 56 is connected to the display controller 22. Further, the image generation unit 21, the display controller 22, the blood vessel detection unit 24, the blood vessel information acquisition unit 25, the needle information acquisition unit 26, the recommended insertion region calculation unit 27, the main body controller 28C, and the puncture position determination unit 56 constitute a processor 32C for the apparatus main body 2C.

The optical camera 55 includes, for example, an image sensor, such as a so-called charge coupled device (CCD) image sensor or a so-called complementary metal-oxide-semiconductor (CMOS) image sensor, and images a body surface of the subject and the ultrasound probe 1 disposed on the body surface BS of the subject to acquire an optical image. The optical camera 55 sends out the acquired optical image to the display controller 22 and the puncture position determination unit 56.

Figure 11:
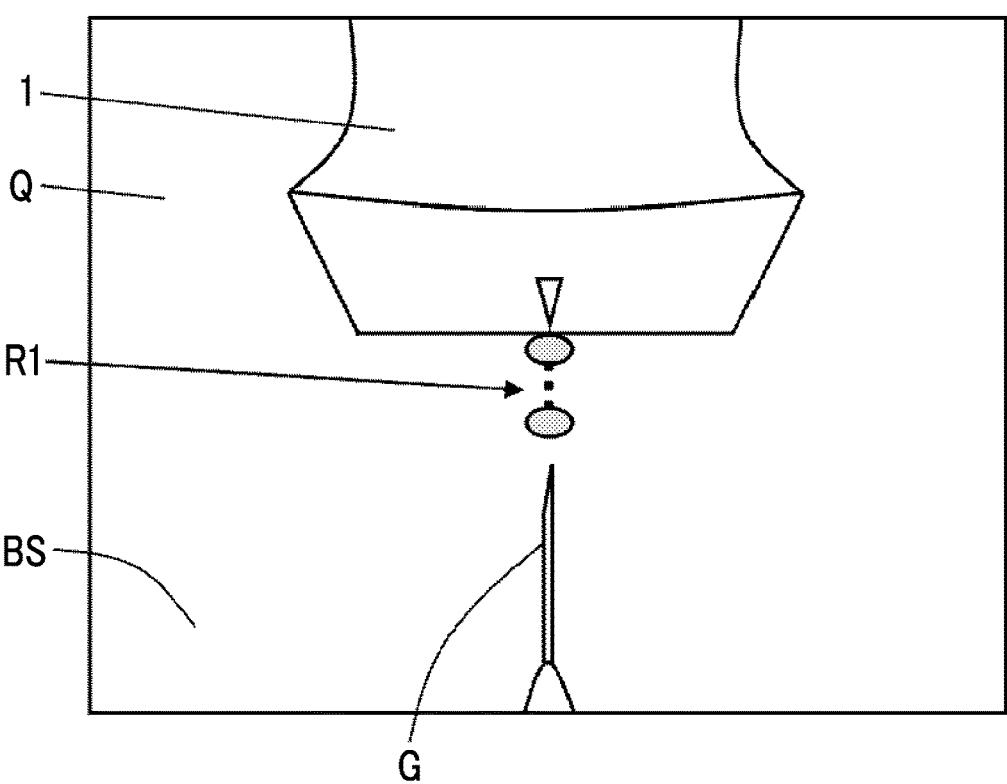
FIG. 11 is a diagram showing an example of a recommended insertion region superimposed on an optical image.

The display controller 22 displays, for example, an optical image Q as shown in FIG. 11 on the monitor 23 together with the ultrasound image U generated by the image generation unit 21. In addition, as shown in FIG. 11, the display controller 22 superimposes and displays a recommended insertion region R1 calculated by the recommended insertion region calculation unit 27 on the optical image Q. The user can easily grasp the position of the recommended insertion region R1 on the body surface BS of the subject by confirming the recommended insertion region R1 superimposed on the optical image Q.

The puncture position determination unit 56 analyzes the optical image Q captured by the optical camera 55 to recognize the body surface BS of the subject and the presence of the puncture needle G, and to determine whether or not the body surface BS of the subject and the puncture needle G, which are recognized, are located within the recommended insertion region calculated by the recommended insertion region calculation unit 27. The puncture position determination unit 56 can determine that the puncture needle G is located within the recommended insertion region, for example, in a case where the tip of the puncture needle G overlaps the recommended insertion region R1 that is displayed by being superimposed on the optical image Q. In addition, the puncture position determination unit 56 can determine that the puncture needle G is not located within the recommended insertion region, for example, in a case where the tip of the puncture needle G is away from the recommended insertion region R1.

Figure 12:
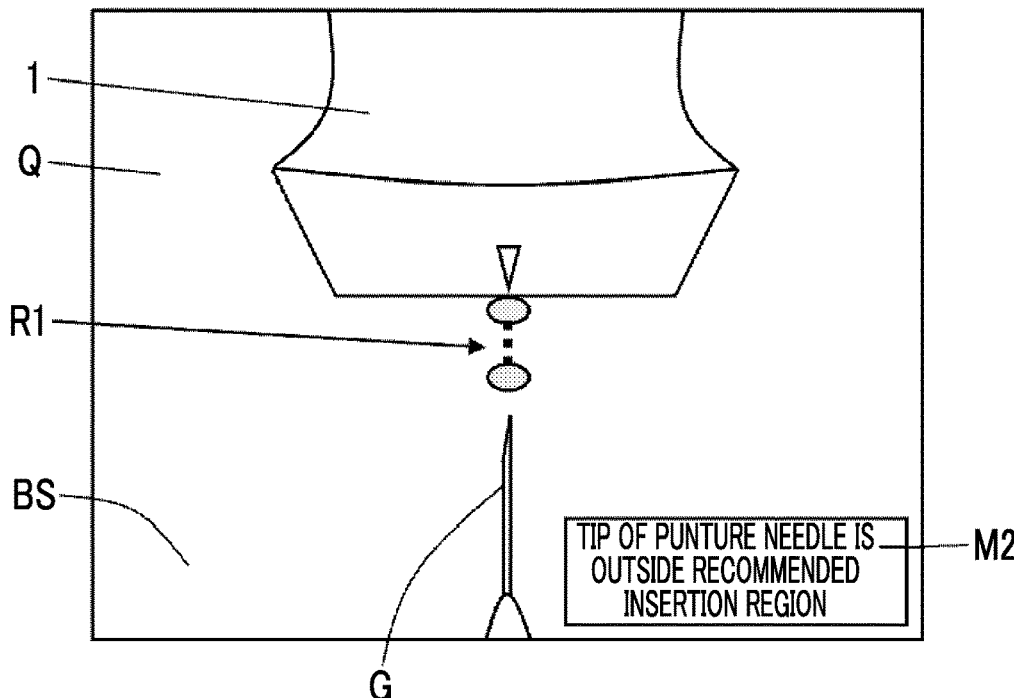
FIG. 12 is a diagram showing a display example of a determination result as to whether the tip of the puncture needle is located inside or outside the recommended insertion region.

The display controller 22 can display the determination result by the puncture position determination unit 56 on the monitor 23, for example, as shown in FIG. 12, through a message M2. In the example of FIG. 12, in the optical image Q, the tip of the puncture needle G is away from the recommended insertion region R1, and the message M2 indicating the determination result that the puncture needle G is not located within the recommended insertion region R1, such as "the tip of the puncture needle is outside the recommended insertion region", is superimposed and displayed on the optical image Q. The user can easily and accurately puncture an appropriate position on the body surface BS of the subject while clearly grasping the current position of the tip of the puncture needle G by confirming the determination result by the puncture position determination unit 56.

From the above, with the ultrasound diagnostic apparatus of Embodiment 4, the recommended insertion region R1 calculated by the recommended insertion region calculation unit 27 is superimposed and displayed on the optical image Q obtained by capturing the body surface BS of the subject and the ultrasound probe 1. Therefore, the user can easily grasp the position of the recommended insertion region R1 on the body surface BS of the subject. In addition, since the display controller 22 displays the determination result regarding the position of the tip of the puncture needle G by the puncture position determination unit 56 on the monitor 23, the user can easily and accurately puncture an appropriate position on the body surface BS of the subject while clearly grasping the current position of the tip of the puncture needle G.

Although the ultrasound diagnostic apparatus of Embodiment 4 has a configuration in which the optical camera 55 and the puncture position determination unit 56 are added to the ultrasound diagnostic apparatus of Embodiment 1, a configuration can also be employed in which the optical camera 55 and the puncture position determination unit 56 are added to the ultrasound diagnostic apparatus of Embodiment 2 and the ultrasound diagnostic apparatus of Embodiment 3.

Embodiment 5

The ultrasound diagnostic apparatus of the embodiment of the present invention can also perform so-called projection mapping, in which the recommended insertion region R1 calculated by the recommended insertion region calculation unit 27 is projected onto the body surface BS of the subject.

Figure 13:
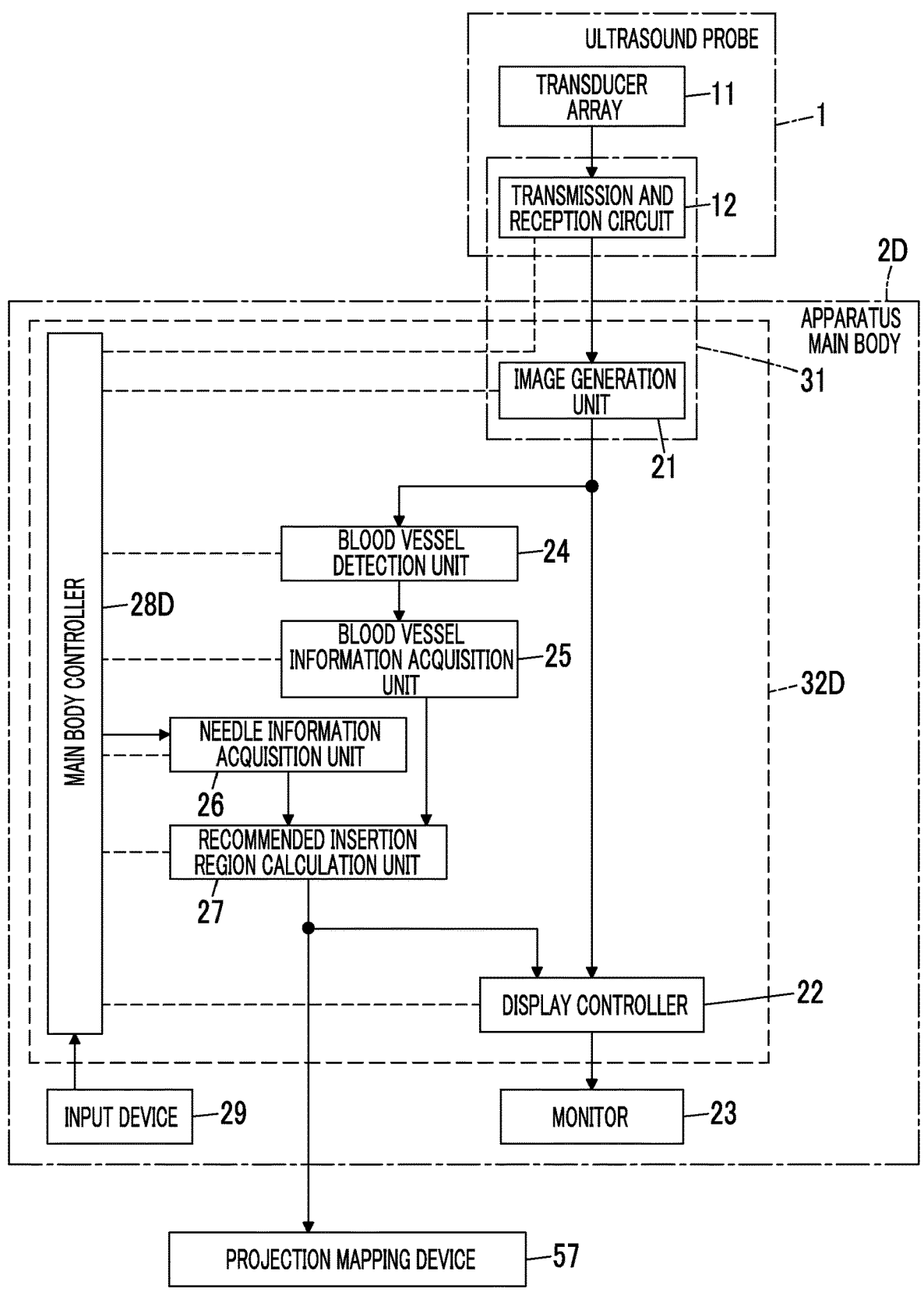
FIG. 13 is a block diagram showing a configuration of an ultrasound diagnostic apparatus according to Embodiment 5 of the present invention.

FIG. 13 shows a configuration of an ultrasound diagnostic apparatus of Embodiment 5. The ultrasound diagnostic apparatus of Embodiment 5 further comprises a projection mapping device 57 and comprises an apparatus main body 2D instead of the apparatus main body 2, with respect to the ultrasound diagnostic apparatus of Embodiment 1 shown in FIG. 1. The apparatus main body 2D comprises a main body controller 28D instead of the main body controller 28 with respect to the apparatus main body 2 in Embodiment 1.

The projection mapping device 57 is connected to the recommended insertion region calculation unit 27 of the apparatus main body 2D. Further, the image generation unit 21, the display controller 22, the blood vessel detection unit 24, the blood vessel information acquisition unit 25, the needle information acquisition unit 26, the recommended insertion region calculation unit 27, and the main body controller 28D constitute a processor 32D for the apparatus main body 2D.

The projection mapping device 57 projects the recommended insertion region R1 calculated by the recommended insertion region calculation unit 27 onto the body surface BS of the subject.

From the above, with the ultrasound diagnostic apparatus of Embodiment 5, the user can accurately insert the puncture needle G into the recommended insertion region R1 by clearly grasping the position of the recommended insertion region R1 while confirming the recommended insertion region R1 projected onto the body surface BS of the subject.

Although the ultrasound diagnostic apparatus of Embodiment 5 has a configuration in which the projection mapping device 57 is added to the ultrasound diagnostic apparatus of Embodiment 1, a configuration can also be employed in which the projection mapping device 57 is added to the ultrasound diagnostic apparatus of Embodiment 2, the ultrasound diagnostic apparatus of Embodiment 3, and the ultrasound diagnostic apparatus of Embodiment 4.

Embodiment 6

In general, depending on the examination, the puncture may be performed in a state in which the body surface BS of the subject is compressed by the ultrasound probe 1. In this case, the shape and the depth D of the blood vessel B to be punctured are changed as compared with those before compression. The ultrasound diagnostic apparatus of the embodiment of the present invention can accurately calculate the recommended insertion region R1 even in a case where the shape and the depth D of the blood vessel B are changed in this manner.

Figure 14:
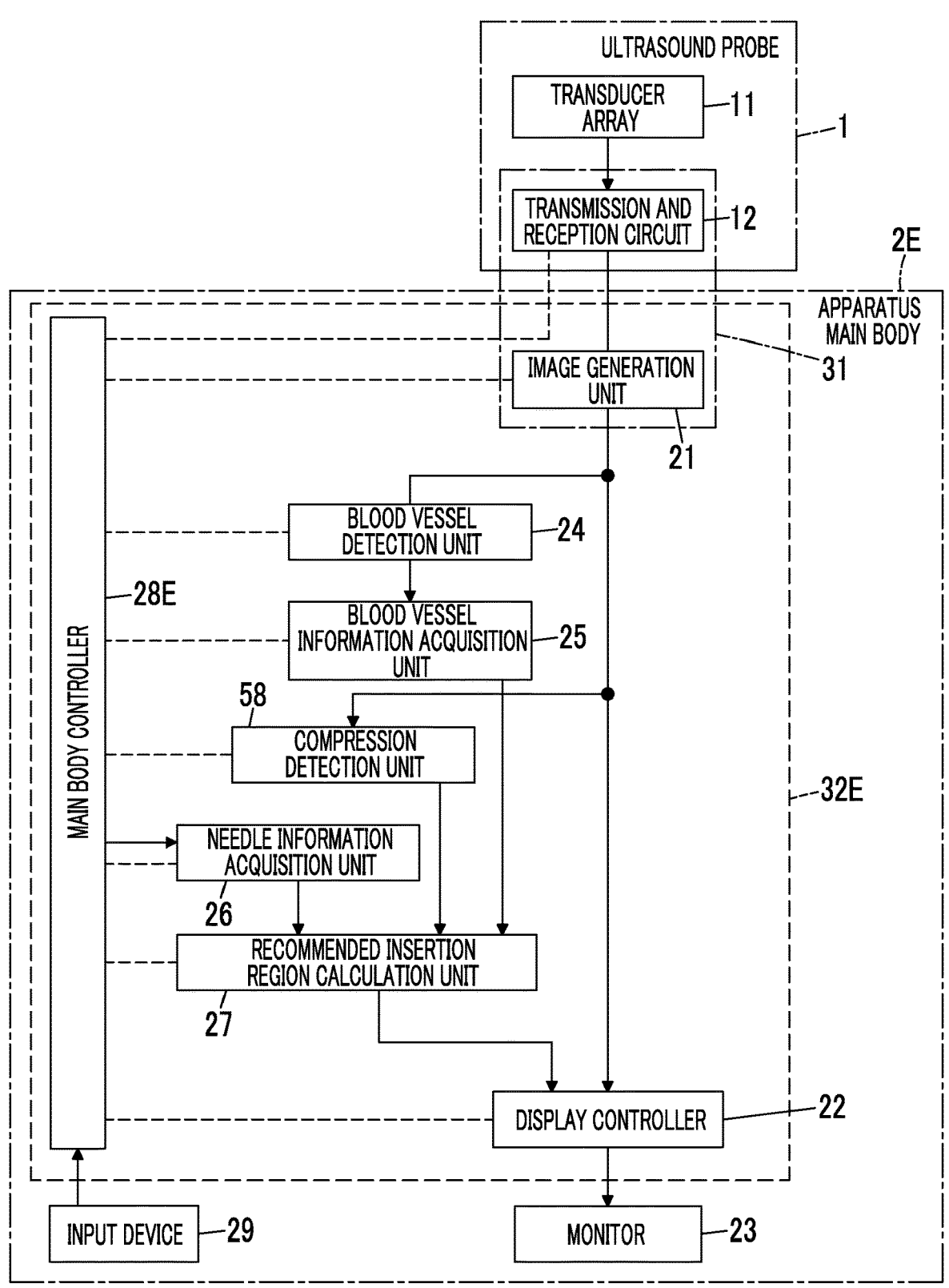
FIG. 14 is a block diagram showing a configuration of an ultrasound diagnostic apparatus according to Embodiment 6 of the present invention.

FIG. 14 shows a configuration of an ultrasound diagnostic apparatus of Embodiment 6. The ultrasound diagnostic apparatus of Embodiment 6 comprises an apparatus main body 2E instead of the apparatus main body 2 with respect to the ultrasound diagnostic apparatus of Embodiment 1 shown in FIG. 1. The apparatus main body 2E further comprises a compression detection unit 58 and comprises a main body controller 28E instead of the main body controller 28, with respect to the apparatus main body 2 in Embodiment 1.

In the apparatus main body 2E, the compression detection unit 58 is connected to the image generation unit 21 and the main body controller 28E. The compression detection unit 58 is connected to the recommended insertion region calculation unit 27. Further, the image generation unit 21, the display controller 22, the blood vessel detection unit 24, the blood vessel information acquisition unit 25, the needle information acquisition unit 26, the recommended insertion region calculation unit 27, the main body controller 28E, and the compression detection unit 58 constitute a processor 32E for the apparatus main body 2E.

The compression detection unit 58 detects the compression on the body surface BS of the subject by the ultrasound probe 1. In general, it is known that, in a case where the body surface BS of the subject is compressed by the ultrasound probe 1, the vein, surrounding tissues, and the like are deformed so as to be compressed in the depth direction, and their positions also move to the deep side. The compression detection unit 58 analyzes, for example, a plurality of continuous frames of ultrasound images U generated by the image generation unit 21, and calculates a compression value representing the degree of compression based on the changes in the shapes and the positions of the blood vessel B and of the surrounding tissues. The compression detection unit 58 can detect that the compression is performed by the ultrasound probe 1, for example, in a case where the compression applied to the body surface BS of the subject is equal to or greater than a predetermined compression value.

Here, in a case where the body surface BS of the subject is compressed by the ultrasound probe 1, the shape and the position of the blood vessel B change, so that the position of the recommended insertion region R1 also changes.

The blood vessel information acquisition unit 25 acquires the blood vessel information of the blood vessel B newly detected by the blood vessel detection unit 24, in a case where the compression detection unit 58 detects that the compression applied to the body surface BS of the subject is equal to or greater than the predetermined compression value.

The recommended insertion region calculation unit 27 recalculates the recommended insertion region R1 based on the blood vessel information newly acquired by the blood vessel information acquisition unit 25 and the needle information of the puncture needle G acquired by the needle information acquisition unit 26, in a case where the compression detection unit 58 detects that the compression applied to the body surface BS of the subject is equal to or greater than the predetermined compression value.

From the above, with the ultrasound diagnostic apparatus of Embodiment 6, the compression detection unit 58 detects the compression on the body surface BS of the subject by the ultrasound probe 1, and the recommended insertion region calculation unit 27 recalculates the recommended insertion region R1 in a case where the compression detection unit 58 detects that the compression applied to the body surface BS of the subject is equal to or greater than the predetermined compression value. Therefore, the user can easily and accurately puncture the blood vessel B by grasping the position of the recommended insertion region R1 even in a case where the body surface BS of the subject is compressed by the ultrasound probe 1.

Although the ultrasound diagnostic apparatus of Embodiment 6 has a configuration in which the compression detection unit 58 is added to the ultrasound diagnostic apparatus of Embodiment 1, a configuration can also be employed in which the compression detection unit 58 is added to the ultrasound diagnostic apparatus of Embodiment 2, the ultrasound diagnostic apparatus of Embodiment 3, the ultrasound diagnostic apparatus of Embodiment 4, the ultrasound diagnostic apparatus of Embodiment 5.

EXPLANATION OF REFERENCES

1: ultrasound probe
2, 2B, 2C, 2D, 2E: apparatus main body
11: transducer array
12: transmission and reception circuit
21: image generation unit
22: display controller
23: monitor
24: blood vessel detection unit
25: blood vessel information acquisition unit
26: needle information acquisition unit
27: recommended insertion region calculation unit
28, 28A, 28B, 28C, 28D, 28E: main body controller
29: input device
31: image acquisition unit
32, 32A, 32B, 32C, 32D, 32E: processor
41: pulsar
42: amplification section
43: AD conversion section
44: beam former
45: signal processing section

46: DSC
47: image processing section
51: peripheral organ recognition unit
52: puncture difficulty level calculation unit
53: notification unit
54: three-dimensional image generation unit
55: optical camera
56: puncture position determination unit
57: projection mapping device
58: compression detection unit
AW: anterior wall
B: blood vessel
BS: body surface
C: center
D: depth
G: puncture needle
K1, K2, L2: distance
M1, M2: message
L1: length
P: tomographic plane
Q: optical image
R1: recommended insertion region
U: ultrasound image

What is claimed is:

1. An ultrasound diagnostic apparatus that assists in puncturing a blood vessel of a subject, the ultrasound diagnostic apparatus comprising:

a monitor;

an ultrasound probe; and a processor configured to continuously acquire an ultrasound image of the blood vessel using the ultrasound probe, detect the blood vessel from the ultrasound image, acquire blood vessel information of the blood vessel which is detected, acquire needle information of a puncture needle, set a needle insertion angle range in which the puncture needle can reach the blood vessel based on the blood vessel information and the needle information, calculate a recommended insertion region of the puncture needle on a body surface of the subject based on the blood vessel information, the needle information, and the needle insertion angle range, the recommended insertion region being defined as a region extending from one end that is located at a distance corresponding to a lower limit of the needle insertion angle range from a contact position of a tip of the ultrasound probe on the body surface of the subject, to another end that is located at a distance corresponding to an upper limit of the needle insertion angle range from the contact position, display the recommended insertion region on the monitor, calculate a puncture difficulty level in inserting the puncture needle from the recommended insertion region based on:

a comparison result between the lower limit of the needle insertion angle range and a predetermined threshold value;

a thickness of the blood vessel;

a change rate of a shape and a position of the blood vessel;

a type of the puncture needle; and presence of a type of an organ recognized around the blood vessel; and display a message indicating the puncture difficulty level on the monitor, or modify a display form of the recommended insertion region on the monitor according to the puncture difficulty level.

2. The ultrasound diagnostic apparatus according to claim 1,
   wherein the processor is further configured to acquire a depth and a thickness of the blood vessel as the blood vessel information.

3. The ultrasound diagnostic apparatus according to claim 1,
   wherein the processor is further configured to superimpose and display the recommended insertion region on the ultrasound image.

4. The ultrasound diagnostic apparatus according to claim 2,
   wherein the processor is further configured to superimpose and display the recommended insertion region on the ultrasound image.

5. The ultrasound diagnostic apparatus according to claim 1,
   wherein the processor is further configured to notify a user of the puncture difficulty level.

6. The ultrasound diagnostic apparatus according to claim 2,
   wherein the processor is further configured to notify a user of the puncture difficulty level.

7. The ultrasound diagnostic apparatus according to claim 3,
   wherein the processor is further configured to notify a user of the puncture difficulty level.

8. The ultrasound diagnostic apparatus according to claim 5,
   wherein the processor is configured to change a method of displaying the recommended insertion region on the monitor or display a message on the monitor according to the puncture difficulty level.

9. The ultrasound diagnostic apparatus according to claim 5,
   wherein the processor is configured to calculate the puncture difficulty level based on the blood vessel information, the needle information, and the recommended insertion region.

10. The ultrasound diagnostic apparatus according to claim 5,
    wherein the processor is further configured to
    recognize an organ located around the blood vessel from the ultrasound image, and
    calculate the puncture difficulty level based on the recommended insertion region and the organ which is recognized.

11. The ultrasound diagnostic apparatus according to claim 1,
    wherein the processor is further configured to
    generate a three-dimensional image of the blood vessel based on the ultrasound image, and
    calculate the recommended insertion region in consideration of the three-dimensional image.

12. The ultrasound diagnostic apparatus according to claim 2,
    wherein the processor is further configured to
    generate a three-dimensional image of the blood vessel based on the ultrasound image, and
    calculate the recommended insertion region in consideration of the three-dimensional image.

13. The ultrasound diagnostic apparatus according to claim 3,
    wherein the processor is further configured to
    generate a three-dimensional image of the blood vessel based on the ultrasound image, and
    calculate the recommended insertion region in consideration of the three-dimensional image.

14. The ultrasound diagnostic apparatus according to claim 5,
    wherein the processor is further configured to
    generate a three-dimensional image of the blood vessel based on the ultrasound image, and
    calculate the recommended insertion region in consideration of the three-dimensional image.

15. The ultrasound diagnostic apparatus according to claim 1, further comprising:
    an optical camera configured to image the subject and the ultrasound probe to acquire an optical image,
    wherein the processor is further configured to superimpose the recommended insertion region on the optical image and display the recommended insertion region on the monitor.

16. The ultrasound diagnostic apparatus according to claim 1,
    wherein the processor is further configured to
    detect compression on the body surface of the subject by the ultrasound probe, and
    once it is determined that the compression applied to the body surface of the subject is equal to or greater than a predetermined compression value, recalculate the recommended insertion region based on the blood vessel information which is acquired.

17. The ultrasound diagnostic apparatus according to claim 1, further comprising:
    an optical camera configured to image the subject and the puncture needle to acquire an optical image,
    wherein the processor is further configured to
    recognize the body surface of the subject and the puncture needle from the optical image, and
    determine whether or not the body surface of the subject and the puncture needle are located within the recommended insertion region.

18. The ultrasound diagnostic apparatus according to claim 2,
    wherein the processor is further configured to acquire a running state of the blood vessel in addition to the depth and the thickness of the blood vessel as the blood vessel information.

* * * * *